United States Patent
De La Mora et al.

(10) Patent No.: US 8,232,519 B2
(45) Date of Patent: Jul. 31, 2012

(54) COUPLING BETWEEN AXISYMMETRIC DIFFERENTIAL MOBILITY ANALYZERS AND MASS SPECTROMETERS OR OTHER ANALYZERS AND DETECTORS

(75) Inventors: Juan Fernandez De La Mora, New Haven, CT (US); Juan Rus, Boecillo (ES); Jerome J. Schmitt, West Palm Beach, FL (US); Francisco Estevez-Molinero, Madrid (ES)

(73) Assignees: Sociedad Europea de Analisis Diferencial de Movilidad, Madrid (ES); NanoEngineering Corporation, Boca Raton, FL (US)

( * ) Notice: Subject to any disclaimer, the term of this patent is extended or adjusted under 35 U.S.C. 154(b) by 45 days.

(21) Appl. No.: 12/597,185

(22) PCT Filed: Apr. 21, 2008

(86) PCT No.: PCT/EP2008/054823
§ 371 (c)(1),
(2), (4) Date: Mar. 2, 2010

(87) PCT Pub. No.: WO2008/129039
PCT Pub. Date: Oct. 30, 2008

(65) Prior Publication Data
US 2010/0213366 A1 Aug. 26, 2010

Related U.S. Application Data

(60) Provisional application No. 60/925,902, filed on Apr. 23, 2007.

(51) Int. Cl.
*H01J 49/26* (2006.01)
*H01J 49/04* (2006.01)
(52) U.S. Cl. ........ 250/281; 250/282; 250/288; 250/287; 250/290
(58) Field of Classification Search .................. 250/281, 250/282, 288, 290, 287
See application file for complete search history.

(56) References Cited

U.S. PATENT DOCUMENTS
5,606,112 A 2/1997 Flagan et al.
(Continued)

FOREIGN PATENT DOCUMENTS
WO 02/18910 A1 3/2002

OTHER PUBLICATIONS

Winklmayr, W. et al.: "A new electromobility spectrometer for the measurement of aerosol size distributions in the size range from 1 to 1000 nm"; Journal of Aerosol Science, vol. 22, No. 3, 1991, pp. 289-296.

(Continued)

*Primary Examiner* — Nikita Wells
(74) *Attorney, Agent, or Firm* — Hoffman & Baron, LLP (57) ABSTRACT

Prior work on differential mobility analysis (DMA) combined with mass spectrometry (MS) has shown how to couple the output of a planar DMA with the atmospheric pressure inlet of an atmospheric pressure ionization mass spectrometer (APCI-MS). However, because the ion inlet to APCI-MS instruments is a round orifice, while conventional DMA geometries make use of elongated slits, the coupling of both has attained less resolving power or tolerated a smaller sample flow rate than a DMA alone. The present invention overcomes these limitations with an axial DMA of cylindrical symmetry using more than two electrodes. The configuration is related to that previously proposed by Labowsky and Fernández de la Mora (2004, 2006), where ions with a critical electrical mobility are brought into the symmetry axis of the DMA. Ions with this critical mobility are now optimally transmitted into the MS, with much higher resolution than possible in planar DMAs. In a preferred embodiment of this DMA facilitating DMA-MS coupling, one DMA electrode intersecting the symmetry axis is relatively planar.

20 Claims, 7 Drawing Sheets

U.S. PATENT DOCUMENTS

| | | |
|---|---|---|
| 6,259,101 B1 | 7/2001 | Wexler et al. |
| 6,787,763 B2 * | 9/2004 | De La Mora et al. .......... 250/287 |
| 6,977,371 B2 * | 12/2005 | Bateman et al. .............. 250/288 |
| 7,351,960 B2 * | 4/2008 | Belford .......................... 250/288 |
| 7,928,374 B2 * | 4/2011 | Rus-Perez et al. ............. 250/292 |
| 2003/0116708 A1 | 6/2003 | De la Mora et al. |
| 2006/0266132 A1 | 11/2006 | Cheng et al. |
| 2010/0243883 A1 * | 9/2010 | Vidal-De-Miguel .......... 250/282 |

OTHER PUBLICATIONS

Fernandez De La Mora, J. et al.: "Tandem Mobility Mass Spectrometry Study of Electrosprayed Tetraheptyl Ammonium Bromide Clusters"; Journal of the American Society for Mass Spectrometry, Elsevier Science Inc., US, vol. 16, No. 3, May 1, 2005, pp. 717-732.

* cited by examiner

COUPLING BETWEEN AXISYMMETRIC DIFFERENTIAL MOBILITY ANALYZERS AND MASS SPECTROMETERS OR OTHER ANALYZERS AND DETECTORS

REFERENCES

Fernández de la Mora, J., L., de Juan, T. Eichler and J. Rosen (1999), Method and apparatus for separating ions in a gas for mass spectrometry; U.S. Pat. No. 5,869,831 (9 Feb. 1999) and U.S. Pat. No. 5,936,242 (10 Aug. 1999)

Fernández de la Mora J (2002) Diffusion broadening in converging differential mobility analyzers, J. Aerosol Science, 33, 411-437

Fernández de la Mora, J. and J. Rus, The use of Multipole ion guides with rods of small dimensions to concentrate small charged species in a gas at relatively high pressure, U.S. provisional patent application US60/857,231 (Dec. 7, 2006).

Flagan, Richard C. and Zhang, Shou-Hua (1997), Radial differential mobility analyzer. U.S. Pat. No. 5,596,136 (Jan. 21, 1997) and U.S. Pat. No. 5,606,112 (Feb. 25, 1997).

Gamero-Castaño, M. and Fernández de la Mora, A condensation nucleus counter (CNC) sensitive to singly charged subnanometer particles; J. Aerosol Sci., 31, 757-772 (2000).

Guevremont; Roger, Purves; Randy, Parallel plate geometry FAIMS apparatus and method, U.S. Pat. No. 6,806,466

Iribarne, Julio V. and Thomson, Bruce A. (1981) Method and apparatus for the analysis of chemical compounds in aqueous solution by mass spectroscopy of evaporating ions, U.S. Pat. No. 4,300,044, Nov. 10, 1981.

Labowsky; Michael J., Fenn; John B., Yamashita; Masamichi (1985) Method and apparatus for the mass spectrometric analysis of solutions, U.S. Pat. No. 4,531,056, Jul. 23, 1985

Labowsky M., and J. Fernández de la Mora, Novel ion mobility analyzers and filters, J. Aerosol Science, 37(3) 340-362, 2006.

Labowsky, Michael J. and Juan Fernández de la Mora, Ion mobility separation devices, International Application published under the patent cooperation treaty (PCT); PCT publication WO2004/077016; PCT/US2004/005133; Sep. 10, 2004

Pourprix, M. (1992). Electrostatic detector of aerosol particles. U.S. Pat. No. 5,117,190.

Ude, S., PhD Thesis, Yale University, 2004.

Ude, Sven, Juan Fernández de la Mora and Bruce Thomson (2004), Charge-Induced Unfolding of Multiply Charged Polyethylene Glycol Ions Investigated via IMS-MS, paper presented at the 2004 annual meeting of the American Society for mass spectrometry.

Zhang, S. H., Akutsu, Y., Rusell, L. M., & Flagan, R. C. (1995). Radial Differential Mobility Analyzer. Aerosol Science and Technology, 23, 357-372, Zhang, S. H., & Flagan, R. C. (1996). Resolution of the radial differential mobility analyzer for ultrafine particles. J. Aerosol Science, 27, 1179-1200.

FIELD OF THE INVENTION

This invention relates to the analysis of ions by mass spectrometry (MS). More specifically, it describes methods and devices to couple a MS with an analytical instrument referred to as a differential mobility analyzer (DMA), separating ions in space, and placed upstream of the MS. The invention overcomes the loss of DMA resolution resulting in prior art for DMA-MS coupling. The invention may be similarly used to couple a DMA to a second instrument or detector or group of instruments or detectors, not all of which need to be mass spectrometers.

INTRODUCTION AND PRIOR ART

Ion mobility spectrometers (IMS) are instruments that separate ions in a gas according to their electrical mobility Z, defined as the ratio between the average drift velocity $u_d$ through the gas induced in the ion by a external electric field E, and the field itself: $Z=u_d/E$. Z depends on the charge on the ion and its shape, so that its measurement in a given gas at a given pressure and temperature provides specific information about the ion.

An important characteristic of an IMS is its resolving power $R=Z/\Delta Z$, defined as the ratio of the peak width $\Delta Z$ (full width at half maximum, FWHM) over its mean mobility for an ion of sharply defined mobility. The resolving power of IMS systems can be as high as 100 (even larger under special circumstances), whereby they can separate ions with Z values differing by less than 1%. MS, separating ions according to their mass/charge ratio, is capable of much higher resolving power, but it is often desirable to increase this power further, as well as to reduce background noise and to separate ions with identical mass/charge ratio. This end can be served by combining an IMS in series with a MS. Most IMS-MS work has relied on IMS systems separating pulsed ion packets in time. This scheme has great analytical advantages, but it has required the development of complex systems coupling the IMS to the MS. This feature generally precludes the simpler use of commercial mass spectrometers, which have reached a level of reliability and sensitivity very difficult to match by specialized developments. For this reason, there is much interest in the development of INS systems suitable to be coupled to a commercial MS with as few modifications as possible to the vacuum system of the MS itself.

The present invention is concerned principally with mass spectrometers of the atmospheric pressure ionization type (API-MS), where the ions to be analyzed are formed at relatively large pressures, often at atmospheric pressure or near it. Because MS analysis functions in a vacuum, there is a need to transfer these ions from a high to a low pressure, while minimizing the simultaneous transfer of neutral gas species. The first element in this ion transfer system is a small orifice, typically a few hundred microns in diameter, open on one side to the high-pressure region, and open on the other side to the first stage of the vacuum system. This orifice may be a hole drilled on a thin plate, a capillary tube, etc. It will generally be referred to here as the "inlet orifice" to the MS. It is important to note that in all existing API-MS systems his orifice is round. There are in fact important advantages to keeping round at least the vacuum end of the orifice, as this leads to the formation of an axisymmetric supersonic free jet, where axial symmetry simplifies the operations of sampling (skimming) the central portions of the jet into a second differentially pumped vacuum chamber, as well as the design of electrostatic or other focusing systems desirable improve ion transmission efficiency.

Figure 1:
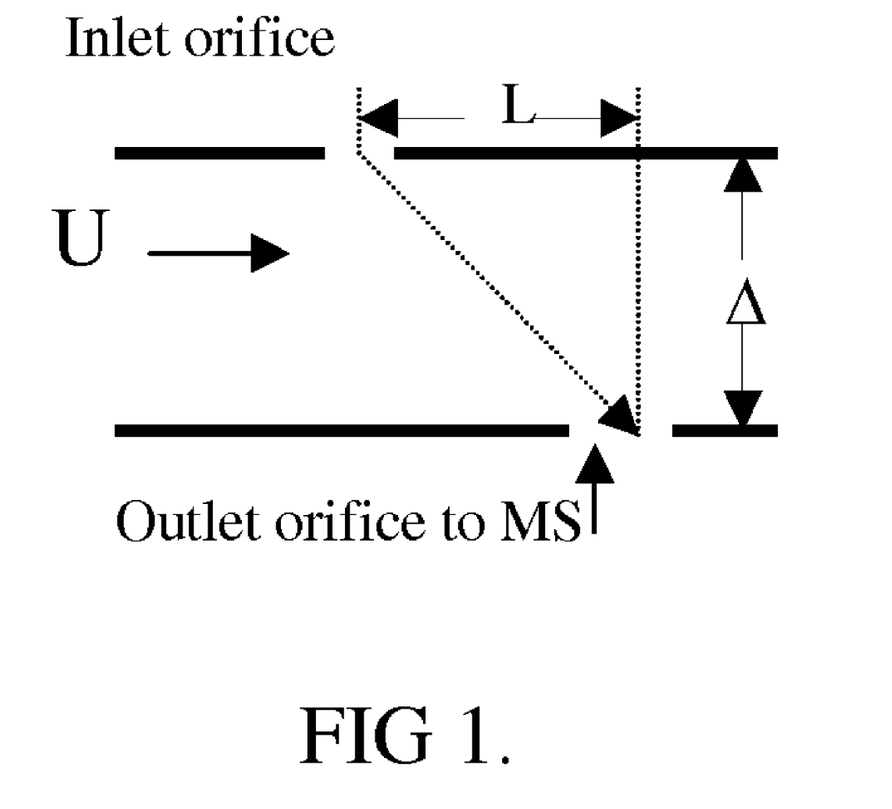
FIG. 1 is a sketch of a planar DMA with sheath gas coming from the left and an electric field driving downwards the ions entering through an inlet slit above, and sampled through the sampling slit below FIG. 2 sketches the axisymmetric DMA OT Labowsky and Fernández de la Mora (2004, 2006).

We have noted the difficulty of coupling pulsed INS systems to commercial API-MS. The coupling is much simpler in INS devices where ions are separated in space rather than in time. Two fairly different such methods have been successfully demonstrated. One is termed Field Asymmetric IMS (FAIMS), as described in U.S. Pat. No. 6,806,466. PAINS relies on slight non-linearities in the relation between the drift velocity of the ion and the external electric field. The other is called Differential Mobility Analysis (DMA), and combines a laminar flow field with an electric field. More specifically, for the purposes of this invention, a DMA is defined as an instrument combining (i) a large laminar flow field of sheath gas produced by a suitable laminarization system with (ii) an electric field generated by several conducting or semiconducting electrodes or grids charged at various points to various electrical potentials, while a narrow stream of ions with various electrical mobilities is injected into the large laminar flow through a narrow inlet orifice or slit with the help of either an electric field or a small flow of gas, (iv) these ions are separated in space according to their electrical mobility, whereby (v) ions of selected electrical mobilities reach one or several sampling or collecting devices. Both DMAs and PAINS instruments can be operated as band-pass filters and transmit to the MS only a small selected class among all the ions ingested. This invention will be concerned with the DMA, which has much higher resolving power than FAIMS, and uses a steady or low frequency high voltage source, much simpler than the corresponding high frequency and high power RAINS voltage source. The first description of a scheme to couple a DMA with a MS with high ion transmission and high resolution is contained in U.S. Pat. No. 5,869,831. While this patent teaches how to achieve high resolution and high ion transmission, an actual instrument able to attain both high resolution and high transmission has not been reported in the 10 year period following patent application. This slow development has not been due to lack of interest in INS-MS coupling. This point is evident from the commercial success of PAINS, in spite of its complex power supply and limited resolving power. The slow development of DNA-MS coupling has been due in substantial measure to several technical difficulties. One initial geometrical problem associated to approximately planar DMAs is the fact that U.S. Pat. No. 5,869,831 gives no details how to arrange the required pair of opposite conducting surfaces separated by insulating surfaces in a fashion avoiding gas leakage between these various parts, and offering very smooth surfaces to the flow so as to avoid turbulence transition at the high Reynolds numbers required for successful operation.

In order to tackle the geometrical problem, a distinction between various DMA types must be made. The type of symmetry exhibited by the DMA and whether or not it matches the symmetry of the MS to which it is to be coupled is important. The symmetry of the inlet hole to the MS is generally cylindrical (a round hole), while the specific DMA-MS high transmission coupling of U.S. Pat. No. 5,869,831 refers to a DMA with planar symmetry. With the exception of the radial DMAs of Flagan, et al. (1997) and of Pourprix (1992), the geometry of the exit region of the DMA (a straight slit or a circular slit) does not match that of the MS, whose inlet orifice has always been circular. We shall not be concerned here with radial DMAs, as they have never shown an ability to attain or even approach the resolving powers desirable for IMS. Subsequent considerations refer therefore to the more conventional family of so called "axial DMAs", where the gas flow enters into the analyzing portions of the instrument in a generally axial direction. U.S. Pat. No. 5,869,831 distinguishes between two kinds of axial DMAs: Those having a generally planar geometry, and those having a generally circular cross-section. The well-known principle of DMA operation is sketched in FIG. 1 for a planar DMA, where ions injected on a linear slit on the upper planar electrode (the inlet slit) are carried to the right by the gas flow at velocity U, and to the bottom by the electric field E at velocity ZE, such that the ion trajectories depend on the mobility Z, and only those ions having mobilities close to a special value Z* reach the sampling slit located on the lower planar electrode. The situation for cylindrical DMAs is similar, except that the two planar electrodes are substituted by coaxial cylinders, and the linear slits become now circular. The terms planar and cylindrical DMAs will be used in a loose sense. The plates do not need to be strictly parallel in the planar DMA. The electrodes could be curved in the plane of FIG. 1, while tending to be straight in the direction normal to the drawing. The slits will also be approximately straight. Similarly, the cylindrical DMA could more generally be axisymmetric, with walls curved in the plane of the figure. Although the "planar" and "cylindrical" DMAs are conceptually similar, their geometrical differences warranted a distinction and a separate treatment in U.S. Pat. No. 5,869,831, and the distinction will similarly be maintained here. Planar DMAs have been considered in a recent application claiming the benefit of priority to U.S. Provisional Patent Application No. US60/790,679, filed on Apr. 10, 2006. That application explains the reasons why the coupling of a generally planar DMA with the conventional axisymmetric inlet orifice of an atmospheric pressure ionization mass spectrometer (API-MS) limits greatly either the sample flow rate through the DMA and into the MS, or the DMA resolution. While the approach proposed in US60/790,679 achieves both high transmission and high resolution in the coupling of a generally planar DMA with an API-MS with a sampling flow rate of 0.5 liters/minute, its extension to the case of substantially larger sample flow rates is problematic. For this reason, the present invention will pursue the case of cylindrical DMAs. More specifically, we shall show how a certain type of axisymmetric axial DMA permits high transmission and high resolution in the coupling of a DMA with an API-MS with a sampling flow rate much larger than 0.5 liters/minute.

No high transmission DMA-MS coupling system has yet been proposed for cylindrical DMAs of the axial type, although a partial solution has been proposed for radial DMAs by Zhang et al, (1995, 1996). Here we will pursue DMAs of the axial type, but we must also note the reason why the approach of Zhang et al. (1995, 1996) is unlikely to yield high transmission and high resolution. One difficulty noted by Fernández de la Mora (2002) is the fact that the radial DMA flow is towards the axis, with a decelerating boundary layer near the axis of symmetry where the charged particles are sampled, and this leads to a separation bubble, which at high Reynolds number will be unstable and produce turbulence. A second difficulty is that the entry region to a radial DMA is cylindrical, so that a seamless laminarizing screen based on conventional flat screen cloth is difficult to implement. Also, the form of the exit region of radial DNAs requires turning the flow by 90 degrees within the working region (in fact, right in front of the ion outlet orifice), something that is rather difficult to achieve at high Reynolds numbers without transition to turbulence. Due to these three reasons and possibly to others, radial DMAs have not been widely used, have never shown high resolving power, and will therefore not be considered further for our purposes. Returning to axial type DMAs, the main obstacle to couple them to a MS has been the need to turn the conventional circular sampling slit located on one of the two cylindrical electrodes into a round orifice located at the symmetry axis of the DMA. No method to achieve this goal has been available until very recently.

Figure 2:
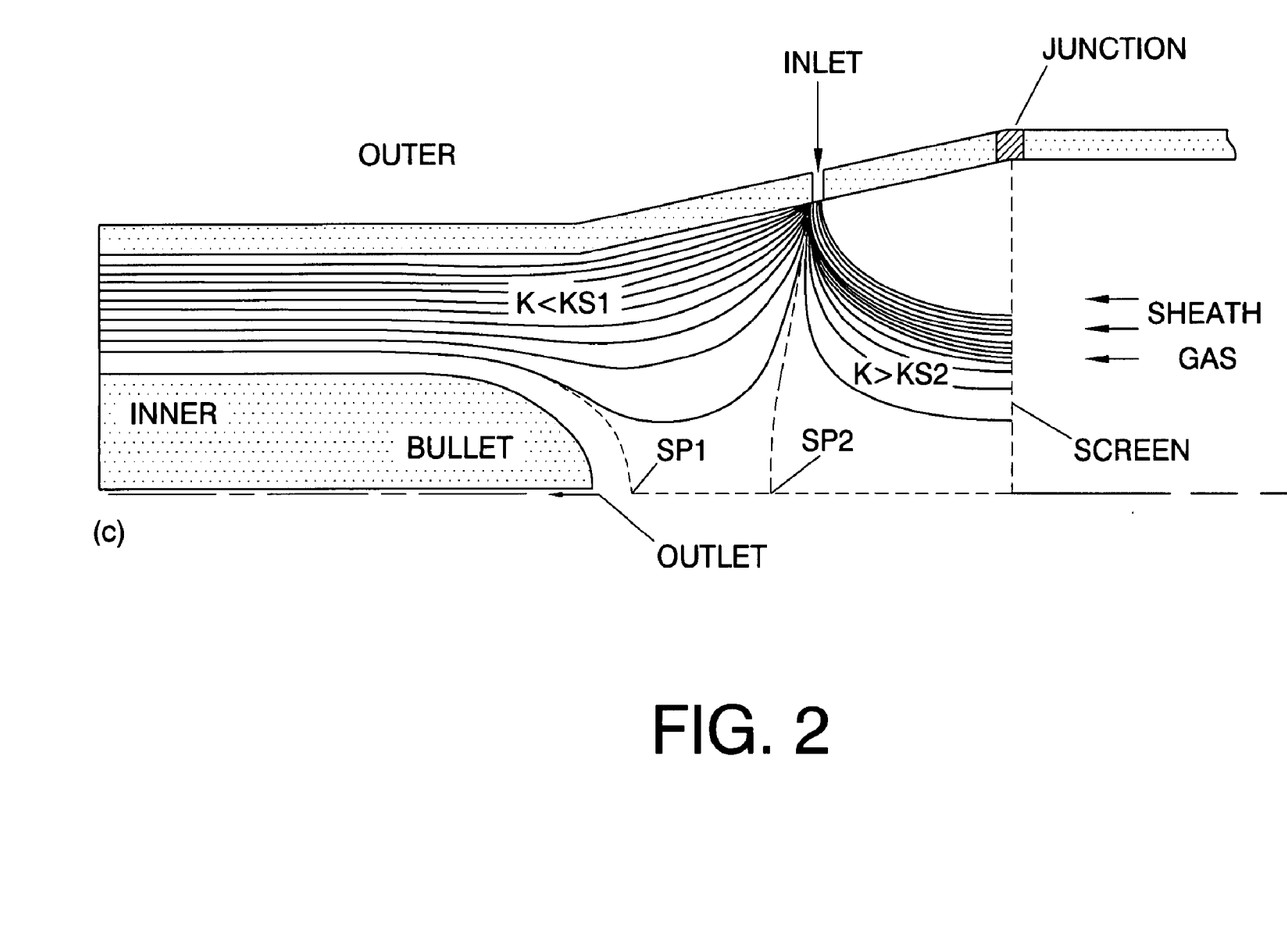

FIG. 2 sketches the axisymmetric DMA of Labowsky and Fernández de la Mora (2004, 2006), whose horizontal axis of symmetry is at the bottom of the figure. The ions are introduced through a circular slit on the outer curved electrode labeled Inlet. They are pulled upstream (to the right) by the electric field generated by an attracting screen and other electrodes located upstream this inlet. But they are simultaneously pushed downstream (leftwards) by the flow of sheath gas. High mobility ions hence move upstream and low mobility ions downstream. At a critical intermediate mobility Z*, the ions go initially neither upstream nor downstream, but head instead towards the axis, where the critical trajectory (broken line) splits at an ion stagnation point, half of the ions going right, the other half left. Under appropriate conditions these critical ions moving downstream proceed along the axis until being sucked into an ion outlet hole drilled on the nose of a bullet-shaped electrode. Labowsky and Fernández de la Mora note that, when the suction applied to the ion outlet exceeds a certain critical value, this outlet samples a narrow range of electrical mobilities, even when the bullet-shaped electrode supporting the ion outlet hole is at the same potential as the outer electrode supporting the ion inlet slit. This device then constitutes a new DMA type, termed an isopotential DMA. A notable advantage of isopotential DMAs is their independence on most prior DMA art, which had generally required establishing a voltage difference between the electrodes supporting the inlet and outlet slits. For the purposes of the present invention, the feature of greatest interest in the Labowsky de la Mora invention is the method taught to bring a ring of ion trajectories into the symmetry axis. Because this ability requires the formation of an ion stagnation point at the axis, we shall refer to such DMAs as stagnation point DMAs (SP-DMAs). One objective of the present invention is to provide a simple solution to the problem of passing a substantial sample flow rate through a DMA and into a MS without losing resolution, by appropriate use of SP-DMAs. Another objective is to introduce improvements on the transmission of ions from a SP-DMA into a MS by means of a new more favorable SP-DMA geometry termed the jet-plate DMA. These two contributions rely on PCT/US2004/005133, but represent new inventions. Indeed, PCT/US2004/005133 is concerned with the problem of DMA-MS coupling only as far as it is facilitated in the special case of isopotential DMAs. Hence, PCT/US2004/005133 does not teach that there is a problem of resolution in conventional DMA-MS coupling, nor hints at the possibility that suitable application of SP-DMAs would solve this problem. The reason why SP-DMAs can indeed solve this problem follows from analysis not taught in PCT/US2004/005133, showing that the resolution of SP-DMAs can be as high as Q/q, where Q is the gas flow rate through the DMA and q is the gas flow rate sampled into the MS through the DMA's ion outlet orifice. This linear-dependence of resolution on Q/q is well known in conventional cylindrical or planar DMAs where the symmetry of the DMA coincides with that of the inlet and outlet slits. But it is new in the case of axial SP-DMAs. In contrast, the maximum resolving power of a planar DMA coupled through an orifice to the circular inlet pinhole of an MS increases only as $(Q/q)^{1/2}$, which is much smaller than Q/q in the usual case when Q>>q. Because the axisymmetric DMAs introduced in PCT/US/2004/005133 were not primarily intended to be coupled to a MS, they suffer from additional problems limiting ion transmission efficiency. This is clear in FIG. 2 from the long distance that the ions ingested through the ion outlet orifice (on the nose of the bullet located at the axis) must travel inside the bullet before they encounter sufficient clearance to be able to be sampled into the inlet to a mass spectrometer. An additional goal of the present invention is to contribute an axisymmetric DMA geometry permitting a close proximity between the ion outlet of a DMA and the MS inlet. Another limitation of the DMA of FIG. 2 when used to sample atmospheric gas is the difficulty to avoid ingestion of neutral contaminating species, drops and particles into the DMA. Vapor contaminants would solvate some of the ions being analyzed in the DMA, evidently complicating the interpretation of the observed mobility peaks, since each ion could appear in many solvation states. These vapors and contaminants could also reach the mass spectrometer, where they would lead to accumulation of dust and malfunctioning. In addition, as taught in U.S. Pat. No. 4,531,056, vapors would condense on many ions in the supersonic free jet forming after the inlet orifice to the MS, and this would further complicate the determination of their mass in the MS spectrum. A final limitation of the DMA of FIG. 2 is the poor ion transmission efficiency of the ions in the region leading to the ion inlet slit. These various difficulties will also be solved in the present invention.

DESCRIPTION OF THE INVENTION

Figure 3:
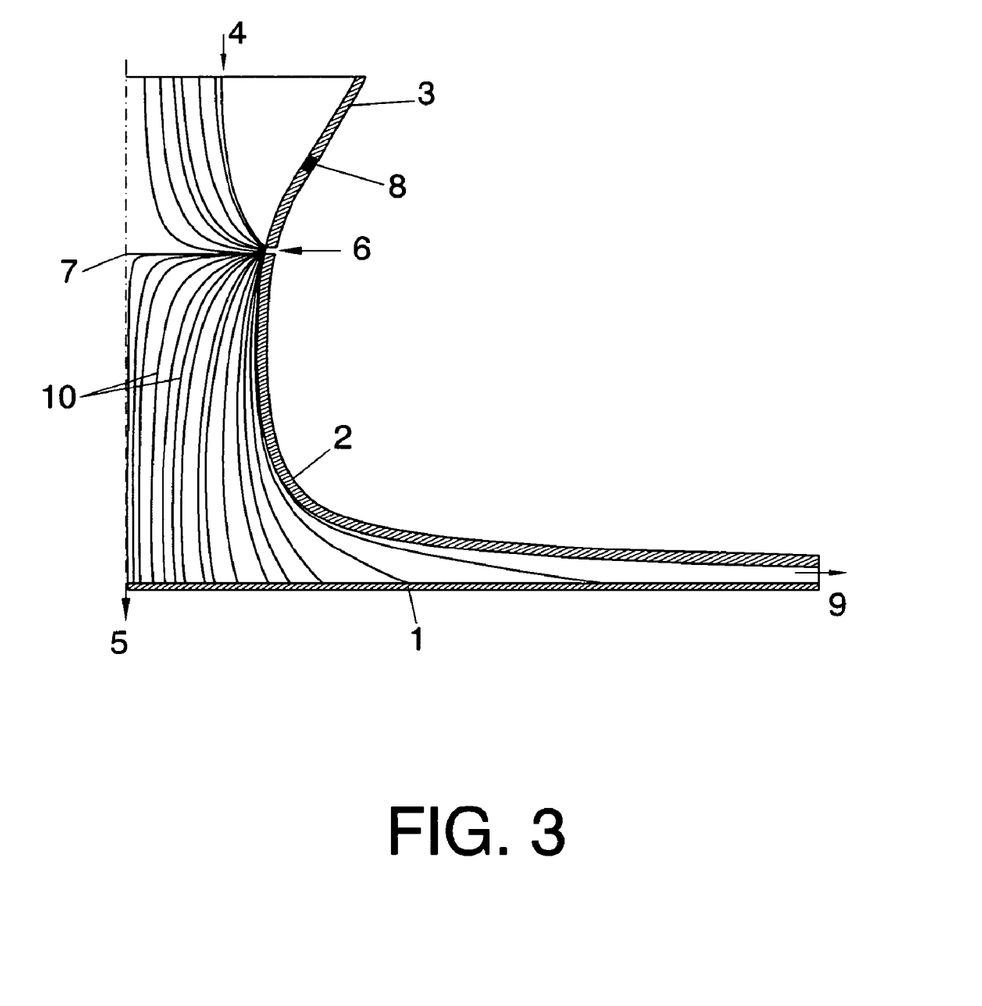
FIG. 3 shows the electrode geometry of an embodiment a jet-plate DMA.

The geometry of the critical flow (wet) surfaces of a preferred embodiment of the invention is shown in FIG. 3 for an axisymmetric axial DMA, where a variant of the method Labowsky and Fernández de la Mora (2004-2006) is used to bring into the close vicinity of the axis all the ions of a critical mobility Z* originating at the inlet slit. One key improvement of the DMA of FIG. 3 over that of FIG. 2 is the substitution of the bullet-shaped electrode supporting the ion outlet orifice by a flat electrode. The new configuration permits close to 100% ion transmission from the DMA outlet into the inlet of the MS, since the flat electrode can be simultaneously the ion outlet of the DMA and the ion inlet to the MS. The same advantage noted in the case of DMA-MS coupling applies to the coupling of a DMA with other analyzers or detectors. In conventional cylindrical DMAs, the length of tubing that the ions must travel from the ion outlet slit into the detector is generally of several cm, leading to relatively high diffusive losses of ions. Even larger distances are generally involved when one couples the mobility-selected outlet of a first DMA into the ion inlet of a second DMA. In the present case, however, a detector or a second analyzing device can be placed immediately downstream the ion outlet orifice. The invention includes also other geometries where the plate is only approximately flat, preserving the same advantage of accessibility of a second instrument to the ion outlet orifice. In one such example the plate would have a modest curvature downwards. In another it would be conical. Many other such situations can be conceived by those skilled in the art without departing from the present invention. However, this invention is not restricted to situations where the first and second instruments are placed immediately after each other, but includes also cases when the ion outlet to the DMA is located at a certain distance from the ion inlet to the subsequent instrument. In such cases, the mobility-selected ions leaving the first instrument would be conveyed to the second by intermediate elements, such as a transfer tube. An even more efficient ion transfer method is an ion guide such as those described in provisional patent application US60/857,231. In these, instead of communicating both instruments with a simple metallic tube, they are communicated with an insulating tube, in whose interior several pairs of wires or poles powered with alternating voltages are placed symmetrically. As a result, the alternating field creates a confinement effect that reduces the losses of the ions to the walls.

The particular cylindrical DMA embodiment shown in FIG. 3 differs from conventional axial DMAs not only in the use of a flat wall electrode [1] normal to the axis, but also in following PCT/US2004/005133 in the use of more than two electrodes [1, 2, 3, 4], some of them [1, 2, 3] charged to different potentials. The bottom flat electrode [1] contains an ion outlet orifice [5] sampling the ions on axis, to relay them with negligible losses to a mass spectrometer or to another analyzer or detector located on the lower side of plate [1]. The bottom plate or wall electrode [1] is generally (but not always) at an electrical potential different from the potential at the surrounding electrode [2], referred to as the lower wall electrode. The resulting electrical attraction from [2] to [1] leads to the arrival of the critical ion trajectory containing ions of mobility Z* into the ion outlet orifice [5] without the need to suction through it a flow rate of gas larger than the threshold value described by Labowsky and Fernández de la Mora (2006). This critical ion trajectory enters the DMA at the ion inlet slit [6], reaches the symmetry axis at the ion stagnation point [7], and then proceeds downwards along the axis. We have noted that the geometry of the bottom electrode [1] is flat in this case, which matches the geometry of several widely used API-MS systems. The presence of this flat electrode poses some serious fluid dynamical challenges, as the flow is forced to bend by 90 degrees, and must do so while remaining laminar at Reynolds numbers generally higher than 10,000, sometimes approaching 100,000. The external electrode wall [2, 3] must therefore be shaped in a special way, such that boundary layer separation along it is avoided. For this purpose, the gas velocity just outside the viscous boundary layer along this wall downstream from [6] must be continuously increasing or approximately constant. Its increase must be slight, however, as otherwise the pressure drop required to produce a high-speed flow would limit the speed (hence the resolution) attainable. Our solution to this problem is to adopt a boundary shape similar to the boundary of an inviscid free jet of fluid colliding perpendicularly against a flat wall. In this case, the jet velocity is exactly constant all the way along the boundary. For this reason, this particular configuration will be referred to as a jet-plate DMA. Note that there is not just one jet-plate DMA, but a wide family of them, corresponding to the many different possible geometries of the nozzle forming the jet, including its exit diameter D and the axial distance L from the nozzle exit to the plate. Because the exit diameter is not well defined for the real viscous problem, it is convenient for the purposes of the discussion to define the DMA throat as the point where the distance between outer wall [2] and the axis is minimal. The throat diameter $D_t$ of the DMA is defined as twice this minimum distance. The Reynolds number of the DMA based on $D_t$, the flow rate Q of sheath gas and the kinematic viscosity ν of the gas under operational conditions will be defined as $$Re=4Q/(\pi D_t \nu).$$

Evidently, viscous effects modify the flow field depending on the value of Re. Another parameter entering the picture, measuring the continuous range of possible compressibility effects, is the ratio $p_o/p_a$ of gas stagnation pressure $p_o$ over background pressure $p_a$ at the nozzle exit. Further freedom in jet shape results from introducing swirl in the inlet flow to the DMA, which can be realized in practice in a multitude of ways. All these geometries and slight variations over them would serve similarly to produce a stable turning flow with modest pressure drop, so they are all included in this invention. Not all ranges of such values are of interest for DMA design. Large pressure ratios would create supersonic flows and shocks, as well as requiring large pumping capacities. However, subsonic, transonic, or moderately supersonic flows are undoubtedly of practical interest. Excessively large L/D values are also undesirable, as mechanical alignment between the various components can be made more precise, and transition to turbulence can be better avoided in short DMAs. The boundary geometry of greatest interest would not be exactly identical to the one computed for an inviscid flow, but it would be relatively close to it in the cases of interest for high resolution ion analysis, where the DMA must be run at very high Reynolds numbers, and viscous effects due to the presence of the DMA wall have relatively weak global effects as long as there is no boundary layer separation. In the design of FIG. 3 there is a laminarization screen [4] defining the DMA inlet at its very top. This screen is metallic and acts also as an electrode. Then follows a wide trumpet shape immediately below the screen. In this upstream region going approximately down to the ion inlet slit [6], the flow is accelerating, and viscous effects are relatively unimportant when the trumpet shape is properly designed. Downstream from the ion inlet opening [6] comes a brief approximately cylindrical region or throat, and finally a widening region at relatively small radial distance to the flat bottom plate [1]. Although this final region appears to the eye in FIG. 3 as having a decreasing section, the flow cross-section is actually slowly widening, so that this final domain is acting as a diffuser. The design of this diffuser is very critical to achieve proper pressure recovery and minimize pumping requirements. This region is also important to the operation of the DMA because, if boundary layer separation were to occur, it would ordinarily result in a non-axisymmetric flow, and this feature would propagate upstream and reduce the resolution. The geometry of the electrode [2] shown in the figure is therefore carefully optimized to improve diffuser efficiency and avoid boundary layer separation, so that the shape shown is also considered part of the invention. Those skilled in fluid dynamics could similarly design other comparable geometries, including those associated to other members of the jet/plate families previously discussed. The design of the transition region between the cylindrical portion and the near wall portion is also quite critical, because any resulting loss of flow steadiness and axisymmetry would affect more directly the ion trajectories and reduce DMA resolution.

The electrode configuration pushing the high mobility ions upstream (and enabling the arrival of a critical ion trajectory into the axis) is similar in the embodiment of FIG. 3 from that used in the Labowsky and de la Mora drawing (FIG. 2). It involves an insulating ring (or a very low conductivity ring) [8] separating the two conducting pieces [3] and [2], such that they can be held at different potentials. It is important that the junction between the insulating ring [8] and the adjacent surfaces upstream [3] and downstream [2] from it be very smooth and free from steps that could precipitate transition to turbulence. Small steps that would result from imperfect centering of the various components can be reduced by polishing on a lathe after assembly. Another alternative is to force a small rounded step at each junction, such that the flow cross section decreases in the downstream direction. In the case of a slight misalignment, this system avoids the possibility of negative steps widening locally the flow cross section, which are a source of vortex shedding and rapid transition to turbulence. The inlet section of the DMA following the laminarization screen [4] includes a converging segment [3] to be referred as the upper electrode. In the embodiment of FIG. 3, [3] is a conductor and is held at the same electrical potential as the screen [4]. In another configuration shown in FIG. 4, the insulator [8] extends all the way from the top end of electrode [2] into the screen [4]. This alternative arrangement permits establishing a larger voltage difference between the electrode [2] and the screen [4] without sparking, with increased electric fields pulling upstream the high mobility ions. The overall geometry shown in FIG. 3 has been optimized via fluid dynamic design such as to avoid boundary layer separation, to minimize the pressure drop for a given flow, and to achieve a substantial pressure recovery in the downstream section of the instrument (which acts as a diffuser). Many variants of this invention can be conceived by those skilled in the art, for instance, introducing curvature into the bottom electrode supporting the sampling orifice, or with other electrode configurations including two or more surfaces or conducting grids, each charged to a potential different from that of its closest neighboring electrodes, designed to provide an initial upstream motion to the most mobile ions. In the preferred embodiment, ions are drawn into the bottom plate [1] by a voltage difference between it and the outer electrode [2]. One favorable combination of voltages applicable to positive ions would assign approximately 0 Volt to the bottom plate [1], 1000 Volt to the lower wall electrode [2], and several kilovolts negative Volt to the laminarization screen [4] and to the upper electrode [3]. The position of the ion inlet slit and the electrical insulator on the outer electrodes is chosen in FIG. 3 such as to maximize resolution, which is limited mainly due to Brownian diffusion. The exit [9] of the DMA would normally be connected to a pump, preferably through a settling chamber to ensure a closely axisymmetric outlet flow.

The jet-plate DMA described so far uses three different electrodes, while conventional DMA geometries use only two electrodes. Other embodiments of the present invention can therefore be based on a jet-plate geometry such as that of FIG. 3, but with only two rather than three different voltages applied. Two such two-electrode jet-plate DMAs are discussed next.

A second embodiment of the invention based on FIG. 3 uses the same electrical potential on the lower [2] and upper [3] portions of the wall electrode, as well as on the inlet screen. In this case there is no need for an insulator [8], and the outer wall [2, 8, 3] can be made out of a single piece of a conducting material. Also, the screen [4] may be made of insulating rather than metallic cloth. The main operational difference with the DMA of FIG. 3 is the lack of upstream attraction for the most mobile ions, whereby all ions are drawn towards the bottom plate. In particular, no ion having a finite electrical mobility can reach the symmetry axis. However, ions of different mobilities will reach the bottom plate at different radial positions, similarly as the ion trajectories [10] shown in FIG. 3 for the preferred embodiment. This second embodiment then acts in many ways as a conventional axial type DMA, except for the considerable advantage that the bottom plate may now be flat, while it is curved all previously disclosed axial type DMAs. Some of the well-known advantages of radial type DMAs therefore apply in this case without loss of some of the other known advantages axial type DMAs (particularly the ease of installation of the inlet laminarization screen, which can be based on standard flat screen cloth). In this embodiment it is preferable to bring the ion inlet slit [6] closer to the bottom plate in order to increase the intensity of the field at this inlet associated to a fixed voltage difference V between electrodes [1] and [2]. Also, in order to enable a higher value of V without sparking, it is preferable to build part of the diffuser region with an insulating material, so as to avoid the close proximity between both electrodes occurring in the exit region [9]. In one embodiment the lower plate [1] is a conductor up to a radial distances from the axis up to ⅓ of its outer radius, and an insulator on the remaining ⅔.

DETAILED DESCRIPTION OF THE INVENTION

Figure 4:
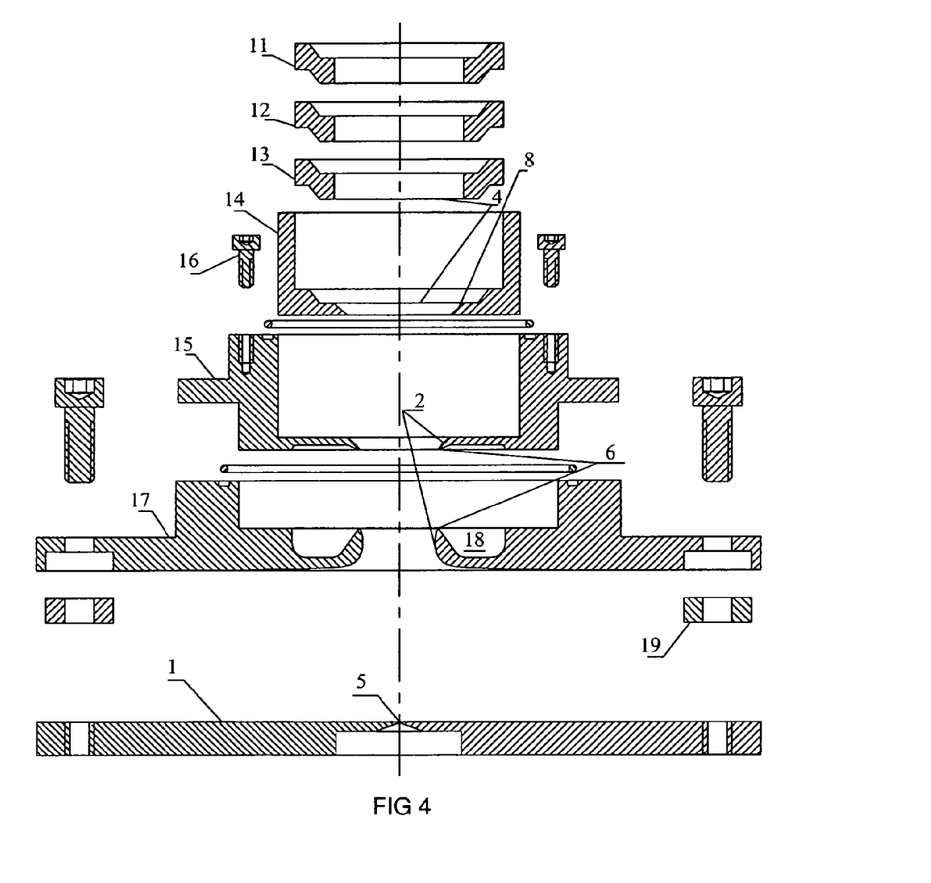
FIG. 4. Shows the mechanical components of a disassembled jet plate DMA prototype

FIG. 4 shows in more detail the components of a jet-plate DMA prototype built, incorporating with slight variations already noted the geometry discussed in relation to FIG. 3. The flow of ion-free sheath gas enters through the top from a cover piece (not shown), and passes through several laminarization screens, each held at the bottom of three screen support rings [11, 12, 13]. These screens are meant to greatly reduce the level of turbulence of the incoming gas stream. The screen holders [11, 12, 13] include several sharp-angled surfaces meant to bring the screen into tension, which is necessary to assure a highly spatially uniform inlet velocity field. The portions of the screen holder rings [11, 12, 13], inclined at 45° from the horizontal and in contact with the screens, may have additional indentations (not shown in the figure) to achieve improved uniformity in screen tension. In FIG. 4, the two screens most upstream may be either of an insulating or a metallic cloth. But the screen [4] placed most downstream is conducting, and is charged to a certain controlled voltage $V_4$ by means not shown in the figure. The screens and their corresponding support rings are inserted into the support piece [14], built out of an insulating material. They are pushed downwards against [14] by means of a top cover piece (not shown), which presses both the screen holders [11, 12, 13] and their support [14] against piece [15], by means of four symmetrically placed fasteners [16]. As a result, proper tension of all the screens and centered location of the various parts described is achieved. Once it goes past the conducting screen [4], the flow of clean gas entering from the top is surrounded on the sides by surfaces [8] and [2] the first of which is an insulator and the second a conductor. Insertion of [15] into [17] completes the definition of the outer walls of the electrode [2] confining the flow, with a thin slit [6] separating the two parts [15] and [17]. Note that assembly of [15] and [17] creates an internal chamber [18], termed the ionization chamber, where ions of substances to be analyzed in the DMA are formed. This internal chamber is communicated with the main flow only through slit [6]. The walls confining the flow are completed by the bottom plate [1], with its centered ion outlet [5], and 8 ceramic separator pieces [19], which fix precisely the axial distance between the electrode surfaces [2] and [1]. The lower electrode [1] is shaped in this case such that it fits into Sciex's 365 triple quadrupole mass spectrometer, very much as its original piece supporting the inlet orifice [5], so that the ion outlet orifice to the DMA coincides with the inlet orifice to the MS, assuring very efficient ion transmission from one to the other.

Some more detail is required about the ionization chamber [18] where the ions to be analyzed are formed and injected through the slit [6] into the flow region of the DMA. We shall consider several embodiments of this ionization step. The first embodiments of the ionization chamber [18] is aimed at producing ions initially dissolved in a liquid. These ions are formed by electrospray (ES) ionization of their solutions, by introducing several ES needles symmetrically arranged around the outer perimeter of chamber [18]. In the preferred embodiment there are 16 such ES needles, entering radially from outside into the interior of the chamber, and aiming their sprays towards slit [6]. The bore of these ES needles is typically 20 to 40 µm, though it may be larger or smaller. The solution fed to each ES needle comes from a single source through a manifold with a bore considerably larger than 40 µm. This ensures that most of the pressure drop is not on the manifold but on the small bore capillaries, so that the flow rate circulating through the 16 ES tips divides itself equally. The high voltage applied to the solution is transmitted through the liquid equally into the 16 tips, which therefore emit their electrosprays symmetrically (same voltage, and same flow rate). The capillary tube emitters are made out of an insulating material, for instance, fused silica, such that the high voltage applied to the solution is not communicated to the surrounding metallic pieces [15] and [17]. This voltage is typically several kilovolts higher than that applied to [15] and [17], so that a field is established inside the ionization chamber, which propels through the gap [6] the ions formed in the ES from analyte substances dissolved in the sprayed solvent. These ions are formed very much as in the electrospray ionization technique introduced in U.S. Pat. No. 4,531,056. Once they reach the middle of the gap [6], they are drawn into the flow region by the strong radial fields prevailing there, principally as a result of the voltage difference established between components [4] and [15]. High ion transmission through the gap in the inlet slit [6] is favored not only by the radial inward fields existing on both sides of the gap, but also by the fact that the gap is wider in the axial than in the radial direction, so that the fields existing inside and outside the gap penetrate through it. The fact that the ions are efficiently driven radially inwards through the gap by electric fields enables the use of countercurrent gas going also through the gap but in the contrary direction (radially outwards). This countercurrent gas is similar to that used in U.S. Pat. No. 4,531,056 to avoid ingestion of vapors and dust or other contaminants into a mass spectrometer through its inlet orifice. In the present case this system avoids the introduction of these undesirable components into the analyzing region of the DMA, and therefore exclude such contaminants also from the mass spectrometer when it is placed downstream from the DMA ion outlet orifice [5]. While humidity in the inlet region to the MS solvates the ions and modifies their mass, humidity inside the analyzing region of the DMA also solvates many of the ions (particularly the smallest ones), vitiating their intrinsic mobility. This complicates the interpretation of the spectra, and also spreads the signal over the mobility range, thus reducing signal intensity. In a slight variant of the ionization system just described, other electrodes are introduced within chamber [18] in the vicinity of the slit [6], with the purpose of creating radial fields even larger than those produced by the electrified capillary tips previously described. A convenient way to control the outflow of countercurrent gas through the inlet slit to the DMA is to operate the DMA in closed loop through a leak-free pump, with its exhaust sheath gas being returned to its inlet sheath gas flow. Injection onto this loop of a net flow rate of clean gas equal to the flow rate q (counterflow) of ions sampled out of the DMA into the MS plus an extra flow rate q' ensures that the extra flow q' exits the inlet slit to the DMA as counterflow gas. Another known advantage of operating the DMA in closed loop is that the level of humidity can be controlled without drying the large flow of ambient air, which would otherwise need to be used as sheath gas.

The third and second embodiments of the ionization chamber [18] are aimed at producing ions from neutral species initially existing in vapor form in a gas. The gas containing these analyte vapors is circulated through this chamber at a certain flow rate q. It enters the chamber [18] through at least one inlet tube, and leaves it through at least another outlet tube, neither of which is shown in FIG. 4. In the second embodiment the same set of symmetrically placed electrospray tips is used, with the main difference that the liquid electrosprayed is a relatively pure solvent made conductive by addition of a certain buffer salt or acid, preferably volatile (such as acetic or formic acids, or ammonium acetate or formate). The charged drops and ions produced by electrospraying this solution then interact with the vapors and charge a certain fraction of them. These ionized vapors are then driven through the gap [6] by the field against the countercurrent gas, and are analyzed in the flow region of the DMA very much as the ions considered in the first embodiment of [18]. In a third embodiment of the ionization chamber [18], the vapors carried in a gas are introduced very much as in the second embodiment. However, the scheme to charge the vapors is no longer based on a discrete number of ES tips, but on a different source of ionizing radiation. This source can be a ring of radioactive Ni-63 located inside the chamber [18] in the vicinity of the slit [6]. It can alternatively be a source of UV radiation, X rays, etc. Like in the other two embodiments of the ionization chamber, counter current gas enters through slit [6] radially outwards into the chamber, so that a radially inward electric field is necessary to drive the ions against the gas flow. This field is created, for instance, by supporting the radioactive Ni ring on an insulating piece and charging it to a voltage higher than, the voltage of pieces [15] and [17]. Alternatively, other ring electrodes at different positions and voltages may be used.

Figure 5:
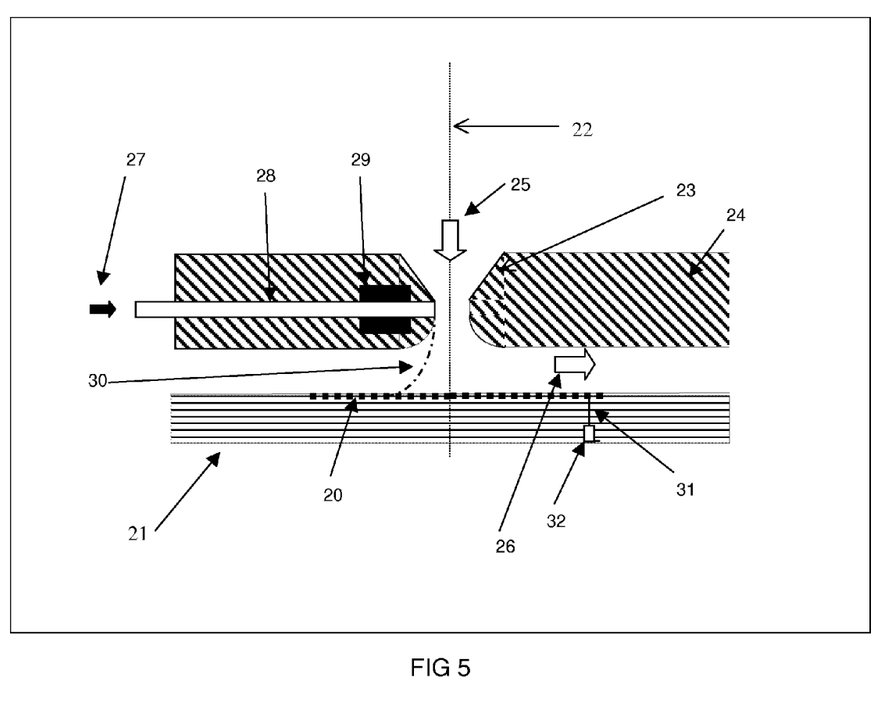
FIG. 5 illustrates the operation of a jet-plate DMA with two electrodes and a large number of detector rings placed on a flat electrode normal to the axis (the wall electrode), to obtain a mobility spectrum without scanning over the voltage.
Figure 6:
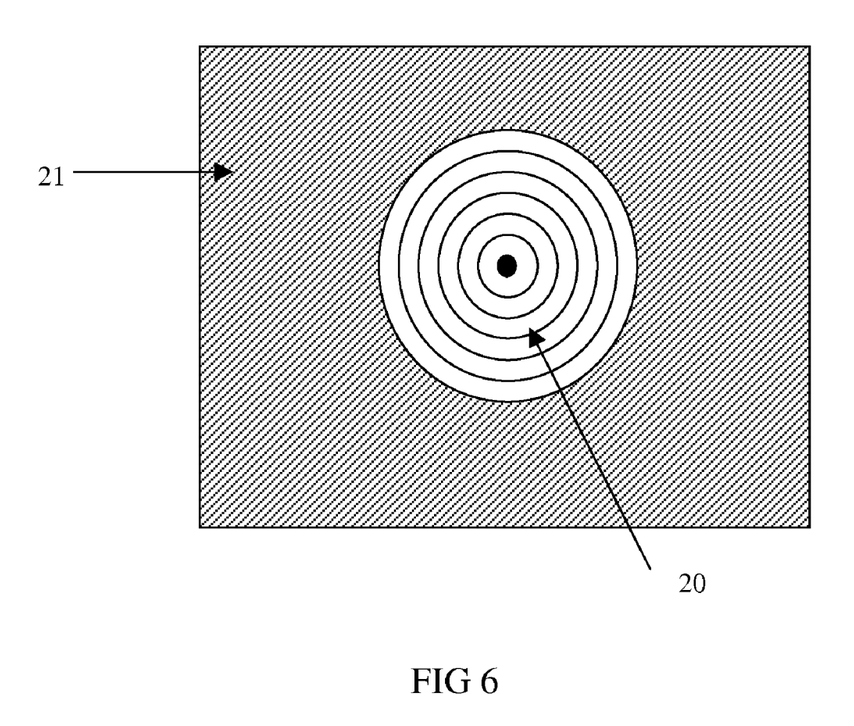
FIG. 6 is a top view of the wall electrode of the Jet-Plate DMA of FIG. 5, showing in more detail one possible arrangement (Bulls-eye pattern) of the Detector Electrode Array
Figure 7:
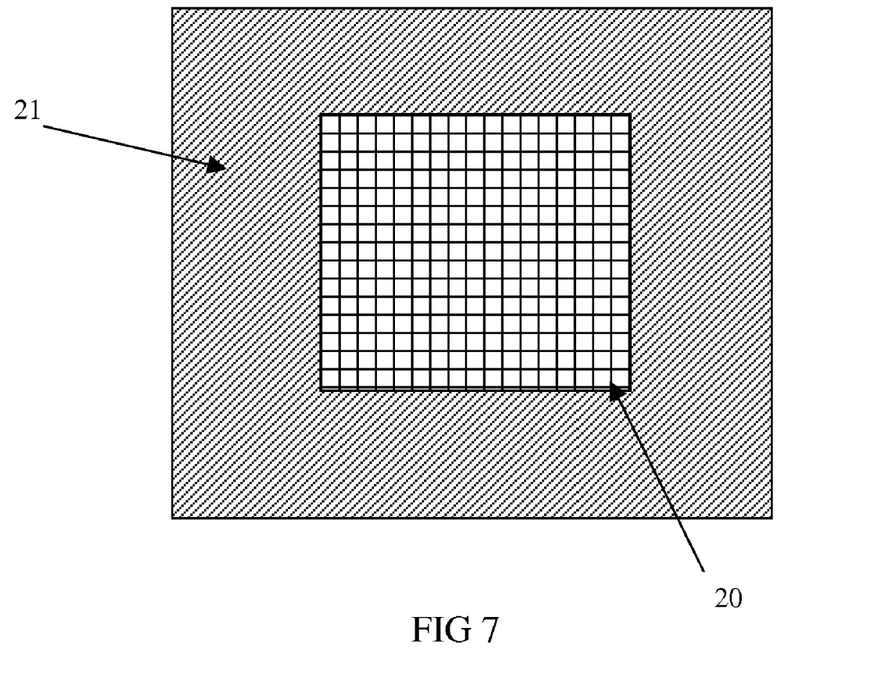
FIG. 7 is a top view of the wall electrode of a Jet-Plate DMA, showing in more detail another possible arrangement (Grid pattern) of the Detector Electrode Array to obtain a mobility spectrum without scanning over the voltage.

One noteworthy advantage illustrated in FIGS. 5, 6 and 7 of having a flat plate electrode in an axial DMA is achieved by placing a large number of closely spaced ring-shaped detectors [20] on an electrically insulating flat bottom plate [21]. These rings are centered around the axis of symmetry [22] of the nozzle [23] in the top plate [24] that accelerates the sheath air flow [25] before it exits the DMA the radial direction [26]. Sample air [27] is introduced into the nozzle [23] via the sample inlet [28] fitted with an ionizer [29] such as a radioisotope. A bias voltage is applied between the plates. The ion abundance associated to a large number of closely spaced electrical mobilities, distinguished by their separate trajectories [30], can be measured simultaneously, each on one ring-shaped detector [20], which is connected to external electrometer circuitry (not shown) via the "buried" leads [31] and associated contact or solder pad [32]. This system of parallel detector electrodes measures an entire mobility spectrum at once, without the need to scan over the voltage, as in conventional DMAs. This multiplicity of detectors can also be implemented in the case of conventional cylindrical electrodes, as shown by prior research of Professor Tammet and colleagues at Tartu University, and as implemented in instrumentation commercialized by the companies TSI and Cambustion. These instruments, however, are not capable of reaching the high resolutions needed for ion mobility analysis. Furthermore, they use a modest number of detectors, which restrict even more their resolving power. These limitations, however, can be overcome in suitably designed DMAs, as previously disclosed to the authors by Jerome J. Schmitt and Wayne Neilson (private communication). However, the possibility to incorporate this multitude of detectors on a flat rather than a curved surface is greatly advantageous from the point of view of applying conventional fabrication and integration techniques of the type used in silicon based electronics. These advantages associated to a flat electrode apply equally in the case of the three electrode embodiments of FIGS. 3 and 4. Note finally that the detector electrodes may actually be shaped as rings, or they may be a two-dimensional grid-array of miniature electrodes (FIG. 7) that are addressed individually by software to define rings. A third embodiment of the present invention containing only two electrodes can be similarly based on the design of FIG. 3. It is a variant of the isopotential DMA of Labowsky and Fernández de la Mora illustrated in FIG. 2. In this case, the bottom electrode and the surrounding wall electrode would both be at the same potential, and could be carved out of one single piece of metal or another conducting material, including silicon. The electrical insulator [8] on the side wall would be preserved, and the upper electrodes [3] and [4] would be charged to a potential such that the ions introduced, through the ion inlet slit would be drawn upstream by the electric field and downstream by the flow field. The result would be a jet-plate variant of the isopotential DMA of Labowsky and Fernández de in Mora, where arrival of ions to the orifice at the axis requires a net suction of gas through the orifice. This third embodiment of the invention has the added advantage over that of FIG. 2 that the flat bottom electrode makes it ideal for coupling to many existing commercial mass spectrometers, whose inlet orifice is carved on a flat surface.

Note that the advantages already discussed for the proposed coupling of a DMA, to a MS apply equally to the coupling of a DMA with instruments other than mass spectrometers. Such an alternative second instrument could be, for instance, an analytical device such as another DMA (for instance operated under conditions where the dragging force exerted by the gas on the ions is non-linear with the drift velocity of the ion through the gas). It could alternatively be a sensing instrument, for instance, a condensation nucleus counter (Gamero and Fernández de la Mora, 2000), which in some cases is capable of sensing individual ions. In each of these cases, the ready accessibility of the outlet region to place the second instrument, and the very small ion losses achieved by this ion exhaust system can be used with great advantage in a variety of applications.

The present invention includes also designs with more than two electrodes (such as the three-electrode configuration of FIG. 3) incorporating also a multitude of ring detectors on the flat bottom electrode (wall electrode), thus providing a mobility spectrum at once. This configuration has the advantage of bringing ions of finite mobility into the near-axis region of the flat bottom plate, which is also the region where the resolution is highest. It has the additional advantage of enabling high-transmission sampling of ions with a specific mobility through an orifice on the axis for a second analysis. The advantage of this combination can be appreciated in the case when the DMA is used to monitor for dangerous or illegal vapors in ambient air. Under routine operation, the instrument would monitor continuously for the appearance of selected substances, which it can do very fast thanks to its ability to obtain full mobility spectra almost instantly. Once an alarm is caused by the detection of a suspicious mobility peak, the flow rate or the voltages in the instrument can be rapidly varied, such that the suspicious ions are directed towards the axis, and sampled through the ion outlet orifice for further analysis (or for more sensitive detection) with a second instrument capable of facilitating confirmation or rejection of the alarm.

The invention claimed is:

1. A method to moderate the loss of resolution associated with sampled flow passing through the ion outlet orifice of a DMA coupled to an analytical instrument having a generally circular inlet orifice, said method comprising:
providing an axial type DMA having an axis of symmetry, said DMA combining a flow of clean sheath gas and electric field to separate ions, and having an ion outlet orifice coincident with said axis of symmetry;
configuring an analyzing region of said DMA such that ions entering said analyzing region are caused to reach said axis of symmetry and to travel along said axis before said ions are sampled into said ion outlet orifice; and,
arranging an analytical instrument such that a generally circular inlet orifice of said analytical instrument receives the flow sampled through the ion outlet orifice of said DMA.

2. A method according to claim 1 where said outlet orifice and said inlet orifice are both part of a single piece of conducting or insulating material.

3. A method according to claim 1 where said ions are driven from said outlet orifice into said inlet orifice by means of an ion guide.

4. A method according to claim 1 where said analytical instrument is a mass spectrometer.

5. A method according to claim 1 where said analytical instrument is a detector of the condensation nucleus counter type.

6. A method according to claim 1 where said outlet orifice is located on a surface generally perpendicular to said axis of symmetry.

7. A DMA apparatus for improved separation of ions, said DMA configured to combine a flow of clean sheath gas and electric field to separate ions, said DMA having an axis of symmetry, a lateral wall, a circular inlet slit for entry of sample ions into the analyzing region of said DMA located on said lateral wall, said lateral wall being generally parallel to said axis of symmetry in the vicinity of said inlet slit, and an ion outlet orifice located on said axis of symmetry and on a relatively flat surface perpendicular to said axis of symmetry.

8. An apparatus according to claim 7 where said lateral wall is curved downstream from said inlet slit so as to be shaped similarly as the boundary of an inviscid axisymmetric free jet of water surrounded by air impinging perpendicularly against a flat plate.

9. An apparatus according to claim 7 including at least one circular ion outlet slit, away from said axis of symmetry, on said relatively flat surface.

10. An apparatus according to claim 7 where at least one point on said lateral wall is charged to a voltage differing from the voltage of at least one point on said relatively flat surface, creating an electric field, such that said ions are separated in space by a combination of entrainment within said sheath gas and drift caused by said electric field.

11. An apparatus according to claim 7 where a portion of said lateral wall is separated by at least one insulating or weakly conducting element from other portions of said lateral wall or from one or several grids, and where various said portions of said lateral wall and one or several grids are charged to various voltages, creating said electric field, such that said ions are separated in space by a combination of entrainment within said sheath gas passing along said axis of symmetry and drift caused by said electric field.

12. An apparatus according to claim 11 where those among said ions having a critical electrical mobility are driven by said combination of entrainment within said sheath gas and drift caused by said electric field first into said axis of symmetry and then into said ion outlet orifice located on said relatively flat surface and from there into a second instrument.

13. An apparatus according to claim 12 where said second instrument is another DMA.

14. An apparatus according to claim 12 where said second instrument is a condensation nucleus counter.

15. An apparatus according to claim 12 where said relatively flat surface is provided with a plurality of ring shaped electrodes or collectors concentric with said symmetry axis, said ring shaped electrodes being electrically insulated from each other, and electrically connected to a current sensing circuit.

16. An apparatus according to claim 15 including means to accept or reject ion identification protocols, whereby trajectories of ions having been identified according to an initial identification protocol are brought to said symmetry axis by suitable control of said voltages and by the magnitude of said sheath gas flow, such that they are sampled through said outlet slit into said second instrument for further analysis.

17. An apparatus according to claim 15 wherein the ring-shaped electrodes or detectors are comprised of ring patterns defined in two-dimensional electrode arrays, wherein array elements are individually addressable and the ring patterns are defined by electronic or software control of the array elements.

18. An apparatus according to claim 7 further including:
  a: means to generate a counterflow gas leaving rather than entering the DMA through an ion inlet slit,
  b: means to create electric fields enabling passage of said ions through said ion inlet slit against said counterflow gas into the interior of said DMA, whereby ingestion through said ion inlet slit into said DMA of low mobility drops and particles, as well as neutral contaminants is avoided, while analysis of said ions is enabled.

19. An apparatus to analyze volatile vapors present in a gas including: an apparatus according to claim 18, and further including means to ionize said volatile vapors immediately upstream of an ion inlet slit permitting entry of ions into the interior of said DMA.

20. An apparatus according to claim 19 where said means to ionize said volatile vapors include at least one electrospray source or a radioactive source.

* * * * *

UNITED STATES PATENT AND TRADEMARK OFFICE
CERTIFICATE OF CORRECTION

PATENT NO.         : 8,232,519 B2  
APPLICATION NO.    : 12/597185  
DATED              : July 31, 2012  
INVENTOR(S)        : Juan Fernandez De La Mora et al.

Page 1 of 1

It is certified that error appears in the above-identified patent and that said Letters Patent is hereby corrected as shown below:

In The Specification

Column 2, line 35, replace "development of INS systems" with --development of IMS systems--.

Column 2, line 51, replace "systems his orifice is" with --systems this orifice is--.

Column 2, line 60, replace "pulsed INS systems" with --pulsed IMS systems--.

Column 2, line 62, replace "in INS devices" with --in IMS devices--.

Column 2, line 65, replace "PAINS relies on" with --FAIMS relies on--.

Column 3, line 15, replace "PAINS instruments can be" with --FAIMS instruments can be--.

Column 3, line 21, replace "power RAINS voltage source" with --power FAIMS voltage source--.

Column 3, line 29, replace "INS-MS coupling" with --IMS coupling--.

Column 3, line 30, replace "success of PAINS in spite of" with --success of FAIMS in spite of--.

Column 3, line 31, replace "development of DNA-MS coupling" with --development of DMA-MS coupling--.

Column 4, line 49, replace "radial DNAs requires" with --radial DMAs requires--.

Column 6, line 23, replace "DMA OT Labowsky" with --DMA of Labowsky and--.

Signed and Sealed this  
Twenty-ninth Day of March, 2016

Michelle K. Lee  
*Director of the United States Patent and Trademark Office*